US00PP16707P2

(12) United States Plant Patent
Zary

(10) Patent No.: US PP16,707 P2
(45) Date of Patent: Jun. 20, 2006

(54) SHRUB ROSE PLANT NAMED 'JACBELGO'

(50) Latin Name: *Rosa hybrida*
Varietal Denomination: JACbelgo

(75) Inventor: Keith W. Zary, Agoura Hills, CA (US)

(73) Assignee: Jackson and Perkins Wholesale, Inc., Medford, OR (US)

( * ) Notice: Subject to any disclaimer, the term of this patent is extended or adjusted under 35 U.S.C. 154(b) by 14 days.

(21) Appl. No.: 10/969,750

(22) Filed: Oct. 19, 2004

(51) Int. Cl.
*A01H 5/00* (2006.01)

(52) U.S. Cl. ..... Plt./104
(58) Field of Classification Search ..... Plt./104, Plt./145, 134
See application file for complete search history.

(56) References Cited

PUBLICATIONS

Barcelona Verda, Noticies [online] No. 87 Apr. 2003 [retrieved on May 4, 2005]. Retrieved on the Internet: <http://www.bcn.es/paracsijardins/cat/publicacions/bcnverda/BCNVERDA_87.pdf>.*
Jackson & Perkins [online] [retrieved on May 4, 2005]. Retrieved on the Internet: <http://www.jacksonandperkins.com/cgi–bin/ncommerce3/ExecMacro/home.d2w/report>.*

* cited by examiner

*Primary Examiner*—Anne Marie Grunberg
*Assistant Examiner*—June Hwu
(74) *Attorney, Agent, or Firm*—Klarquist Sparkman LLP

(57) ABSTRACT

Shrub rose plant having large flowers; very high petal count; strong fragrance; glossy, disease resistant foliage; and ease of propagation from soft and hardwood cuttings.

1 Drawing Sheet

Genus and species: *Rosa hybrida.*
Variety denomination: 'JACbelgo'.

ORIGIN OF THE INVENTION

The present invention relates to a new and distinct variety of a shrub rose plant named 'JACbelgo' which was originated by me by crossing the variety 'JACjubel', U.S. Plant Pat. No. 9,657, with the variety 'AUSgold', U.S. Plant Pat. No. 8,688.

BACKGROUND OF THE INVENTION

The primary objective of this breeding was to produce a new rose variety having the more compact habit, more glossy foliage and disease resistance of the female parent combined with the fragrance and high petal count of the male parent.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Large flowers.
2. Very high petal count.
3. Strong fragrance.
4. Glossy, disease resistant foliage.
5. Ease of propagation from soft and hardwood cuttings.

Asexual reproduction of this new variety by cuttings, as performed at Wasco, Calif., shows that the foregoing and all other characteristics and distinctions come true to form and are established and transmitted through succeeding propagations.

Comparison with Parents

As compared to the female parent 'JACjubel', 'JACbelgo' differs being a larger plant, and having larger flowers, more petals and more fragrance. As compared to the male parent 'AUSgold', 'JACbelgo' differs in being a smaller, more compact plant, and having a different fragrance and more glossy foliage.

Comparison with Similar Variety

A similar variety is 'AUSgold' which is a larger plant, with a different fragrance and less glossy foliage than 'JACbelgo'.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart© 2001, except where ordinary dictionary significance of color is indicated.

Parentage:

*Seed parent.*—'JACjubel' (Mirabella), U.S. Plant Pat. No. 9,657.

*Pollen parent.*—'AUSgold' (Golden Celebration), U.S. Plant Pat. No. 8,688.

FLOWER

Observations made of plants commencing at three years of age in a garden environment at Somis, Calif., from January 2003 to August 2004.

Blooming habit: Continuous.

Bud:

*Size.*—About 3 cm long and 3 cm in diameter when the petals start to unfurl.

*Form.*—The bud form is globular.

*Color.*—When sepals first divide, bud color is Yellow Group 13B often blushed with Red Group 45C. When half blown, the upper sides of the petals are Yellow-Orange Group 15D; and the lower sides of the petals are Yellow-Orange Group 15D.

*Sepals.*—Color: Upper surface: Green Group 138C. Lower surface: Yellow-Green Group 146C. Length: 30 mm. Width: 11 mm. Shape: Subulate. Surface texture: Hoary. There are three normally appendaged sepals. There are two unappendaged sepals with hairy edges.

*Receptacle.*—Color: Yellow-Green Group 146C, often overlain with Greyed-Red Group 178A in areas exposed to bright sun. Shape: Funnel. Size: About 11 mm long×9 mm wide. Surface: Smooth.

*Peduncle.*—Length: Medium, averaging about 40–50 mm. Surface: Smooth. Color: Yellow-Green Group 146D, often colored with Greyed-Red Group 178A in areas exposed to bright sun. Strength: Bending.

Bloom:

*Size.*—Large. Average open diameter is about 10 cm.

*Borne.*—Singly and several together in pyramidal clusters of 3–5 blooms.

*Stems.*—Strength: Strong. Average length is about 40–50 cm with a diameter of 5–8 mm.

*Form.*—When first open: Cupped. Permanence: Flattens.

*Petalage.*—Number of petals under normal conditions: 100–120.

*Color.*—The upper sides of the petals are Yellow-Orange Group 15D. The reverse sides of the petals are Yellow-Orange Group 15D. The base of each petal has a color spot of Yellow-Orange Group 15A, about 2 mm by 2 mm in size. The major color on the upper side is Yellow-Orange Group 15D.

*Variegations.*—None observed.

*Discoloration.*—The general tonality at the end of the first day: No change. At the end of the third day: No change.

*Fragrance.*—Strong, citrus (lemon).

Petals:

*Texture.*—Thin.

*Shape.*—Round to obovate to oblanceolate.

*Surface.*—Smooth.

*Size.*—38×38 mm.

*Margin.*—Entire. Apex Shape: Rounded to cuspidate. Base Shape: Cuneate to attenuate.

*Form.*—Flat.

*Arrangement.*—Quartered.

*Petaloids.*—Number: 5–15. Color: Yellow-Orange Group 15D. Size: 7–25 mm long, 2–10 mm wide.

*Persistence.*—Petals drop off cleanly before drying.

*Lastingness.*—On the plant: Fair (about 5–6 days). As a cut flower: Fair (about 6–7 days).

Reproductive parts:

*Stamens.*—Number: 25–30. Length: 5–6 mm. Anthers: Length: 1–2 mm. Color: Yellow-Orange Group 16B. Arrangement: Regular around styles mixed with petaloids. Filaments: Color: Yellow Group 12C. Length: 4–5 mm. Pollen: Color: Yellow-Orange Group 22B.

*Pistils.*—Number: 40–50. Length: 8–9 mm. Styles: Color: Green-White Group 157D. Length: 7–8 mm. Stigmas: Color: Yellow Group 4C. Length: 1 mm.

*Hips.*—None observed.

PLANT

*Form.*—Shrub.

*Growth.*—Very vigorous, upright, branching.

*Age at maturity.*—Two years.

*Mature plant.*—Height: 120–130 cm. Width: 100–120 cm.

*Rootstock.*—Own root.

Foliage: Number of leaflets on normal mid-stem leaves: 5 or 7.

*Size.*—Large. About 13 cm long×10 cm wide.

*Quantity.*—Abundant.

*Color.*—New foliage: Upper side: Greyed-Red Group 178A. Lower side: Greyed-Red Group 178A. Old foliage: Upper side: Green Group 139A. Lower side: Green Group 137C.

Leaflets:

*Size.*—About 55 mm long×35 mm wide.

*Shape.*—Pointed oval.

*Base shape.*—Oblique.

*Apex shape.*—Acuminate.

*Texture.*—Leathery, glossy.

*Edge.*—Serrated.

*Serrations.*—Single.

*Petiole.*—Color: Yellow-Green Group 146D.

*Surface texture.*—Smooth.

*Petiole rachis.*—Color: Yellow-Green Group 146D. Underside: Smooth.

*Auricles.*—None.

*Stipules.*—Length: 15 mm. Smooth, edged in glands.

*Color.*—Yellow-Green Group 144A.

*Disease resistance.*—Resistant to powdery mildew and rust, susceptible to blackspot under normal conditions.

*Pest resistance.*—Not observed.

*Vein color.*—Green Group 137C.

*Venation pattern.*—Reticulate.

Wood:

*New wood.*—Color: Greyed-Red Group 178B. Bark: Smooth.

*Old wood.*—Color: Yellow-Green Group 146C. Bark: Smooth.

Prickles:

*Quantity.*—On main canes from base: 10 prickles per 15 cm. On laterals from main canes: 10 prickles per 15 cm.

*Form.*—Hooked downward.

*Length.*—9–11 mm.

*Color when young.*—Greyed-Red Group 182A.

*Color when mature.*—Greyed-Orange Group 166C.

Small prickles:

*Quantity.*—On main stalks: None. On laterals: None.

Winter hardiness: Hardy to Zone 5.

I claim:

1. A new and distinct variety of rose plant of the shrub class, substantially as herein shown and described, characterized particularly by its large flowers; very high petal count; strong fragrance; glossy, disease resistant foliage; and ease of propagation from soft and hardwood cuttings.

* * * * *

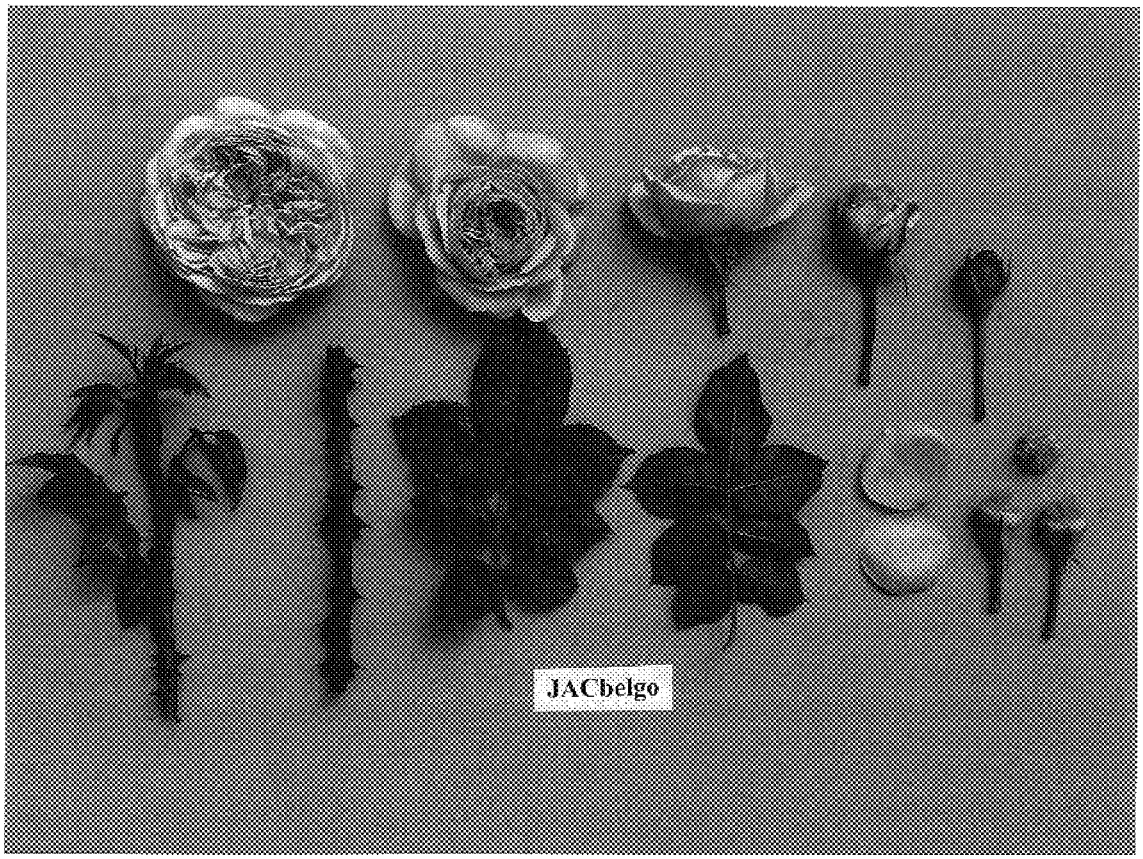
JACbelgo